United States Patent [19]

Bennett et al.

[11] Patent Number: 4,908,205

[45] Date of Patent: * Mar. 13, 1990

[54] STABILIZED HUMAN TISSUE PLASMINOGEN ACTIVATOR COMPOSITIONS

[75] Inventors: William F. Bennett, San Francisco; Stuart E. Builder, Belmont; Larry A. Gatlin, Concord, all of Calif.

[73] Assignee: Genentech, Inc., South San Francisco, Calif.

[*] Notice: The portion of the term of this patent subsequent to Oct. 11, 2005 has been disclaimed.

[21] Appl. No.: 173,854

[22] Filed: Mar. 28, 1988

Related U.S. Application Data

[62] Division of Ser. No. 811,081, Dec. 17, 1985, Pat. No. 4,777,043.

[51] Int. Cl.$^4$ .................. A61K 37/547; A61K 31/195
[52] U.S. Cl. ................................ 424/94.64; 514/561; 514/970
[58] Field of Search ..................... 424/94.64; 514/561, 514/970

[56] References Cited

FOREIGN PATENT DOCUMENTS 0156169 10/1985 European Pat. Off. .
0211592 2/1987 European Pat. Off. .
0217379 4/1987 European Pat. Off. .
2176702 1/1987 United Kingdom .
2176703 1/1987 United Kingdom .

OTHER PUBLICATIONS

Aok; J. Biochem., 75:731, 1974.

*Primary Examiner*—John W. Rollins
*Attorney, Agent, or Firm*—Walter H. Dreger

[57] ABSTRACT

Disclosed are novel, stable pharmaceutically acceptable compositions containing human tissue plasminogen activator, featuring, for example, an argininium ion containing buffer as a component. Also disclosed are associated means and methods for preparing and using such compositions in various forms.

17 Claims, 3 Drawing Sheets

STABILIZED HUMAN TISSUE PLASMINOGEN ACTIVATOR COMPOSITIONS

This application is a division of application Ser. No. 06/811,081, filed 17 Dec. 1985, now U.S. Pat. No. 4,777,043.

FIELD OF THE INVENTION

The present invention is directed to pharmaceutical compositions containing the protein human tissue plasminogen activator (t-PA) and to methods for making and using such compositions. More particularly, this invention relates to such pharmaceutical compositions having increased stability and solubility characteristics for the t-PA component, and those affording ready lyophilizability, making possible the ability to create stable, lyophilized forms thereof for safe, effective therapeutic administration to human subjects.

BACKGROUND OF THE INVENTION

The instability of vascular plasminogen activator extracted from the vascular trees of human cadavers is described by Aoki, J. Biol. Chem. (Tokyo), 75, 731 (1974). Aoki found that the activator was stabilized only by high sodium chloride concentrations, greater than about 0.5M.

Binder, et al. J. Biol. Chem. 254, 1998 (1979) describe the use of high salt and arginine containing buffers during a multi-step purification procedure as essential to maintain the activity of vascular plasminogen activator derived from human cadaver perfusates. The purification steps where carried out in the presence of 0.3 to 1.0M NaCl and 0.1M arginine.

Radcliffe et al., Arch. of Biochem. & Biophy. 189, 185 (1978) describe the separation of plasminogen activator from human plasma by chromotography on lysine-Sepharose. In one experiment, crude plasminogen activator from stabilized plasma was eluted from lysine-Sepharose using a gradient of 0M to 0.5M arginine in 0.6M NaCl.

Human tissue plasminogen activator derived from natural tissue source is described by Collen et al. in European Patent Application Publication No. 041766, published Dec. 16, 1981 based upon a first filing of June 11, 1980. The authors employed a purification scheme that affords tissue plasminogen activator at relatively high purity levels. Collen et al. studied the stability of preparations of their purified tissue plasminogen activator both in the liquid and lyophilized states, and found that the lyophilized forms were repeatedly unstable even when prepared from solutions containing 0.3M NaCl.

In order that materials like tissue plasminogen activator be provided to health care personnel and patients, these materials must be prepared as pharmaceutical compositions. Such compositions must be stable for appropriate periods of time, must be acceptable in their own right for administration to humans, and must be readily manufacturable. An example of such a composition would be a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the medicinal agent contained in the composition under a wider variety of storage conditions, as it is recognized by those skilled in the art that lyophilized preparations are generally more stable than their liquid counterparts. Such lyophilized preparations are reconstituted prior to use by the addition of suitable pharmaceutically acceptable diluent(s), such as sterile water for injection or sterile physiological saline solution, and the like.

SUMMARY OF THE INVENTION

It is an object of the present invention to prepare stable compositions of human tissue plasminogen activator, particularly those in stable, lyophilized form.

The present invention is based upon the discovery that the inclusion of arginine (as argininium ion) in a pharmaceutically acceptable composition of tissue plasminogen activator (t-PA) significantly increases the stability and solubility of t-PA, and further, together with a choice of suitable counterions, makes possible the preparation of stable, lyophilized forms thereof. The invention is thus directed to such compositions and to all associated equivalents and to means to effectively produce such compositions and equivalents.

In general, the compositions may contain other components in amounts preferably not detracting from the preparation of stable, lyophilizable forms and in amounts suitable for effective, safe pharmaceutical administration.

Suitable pH ranges for the preparation of the compositions hereof are from about 4 to about 9, preferably, as these compositions are designed for pharmaceuticals, in the physiological pH span, i.e., about neutral. In this pH range arginine exists primarily as a protonated cation with net charge +1, which can be termed "argininium ion". The term "arginine" is used interchangeably herein with "argininium ion" because due to pH of system, "argininium ion" is an equivalent description. To retain electrical neutrality, the argininium ion must be balanced by an equivalent amount of oppositely charged (i.e. negatively charged) ionic species, which can be termed "counterions". The combination of argininium ion, other cationic species, and the various counterions can be termed an "argininium ion-containing buffer system". Acceptable counterions include those that are pharmaceutically acceptable and additionally those that are capable of adjusting the apparent eutectic or collapse temperature of the composition such that the composition is particularly suited for ready lyophilization. Examples of such counterions are acetate, phosphate, citrate, succinate, sulfate, tartrate, malate, maleate, carbonate, and the like, as well as functional equivalents thereof. An example of a counterion that is not well suited is chloride ion.

As stated above, the inventors have found that inclusion of arginine (as argininium ion) in pharmaceutical compositions of t-PA markedly increases the solubility and stability of the t-PA in these compositions. Arginine concentrations may range from about 0.02M to 1M, preferably from about 0.05M to about 1.0M and more preferably from about 0.1M to about 0.5M in the administered solution, and/or, in the case of a lyophilized preparation, in the prelyophilization solution.

Additionally, the improved compositions may optionally include one or more nonionic detergents, such as polysorbate 20 and polysorbate 80 and the like, in amounts of about 0.001 to about 1 percent, in order to enhance further the stability of the t-PA. In addition, other pharmaceutically acceptable excipients well known to those skilled in the art may also form a part of such compositions. These can include, for example, various bulking agents, additional buffering agents, chelating agents, antioxidants, preservatives, cosolvents, and the like; specific examples of these could include mannitol, tromethamine salts ("Tris buffer"), disodium edetate, gelatin, human serum albumin or other polypeptides, various small peptides such as glycylglycine, and so forth.

The t-PA compositions of the present invention surprisingly do not require the use of high concentrations of sodium chloride, i.e., about 0.3M or above. In fact, high concentrations of chloride ion are detrimental to the lyophilizability of these improved compositions. Although some amount of chloride ion is tolerated, low concentrations are preferred, e.g., less than about 0.3M and are preferably not greater than normal physiological levels i.e., about 0.12M NaCl. Most preferably, chloride ion is excluded from the composition.

A "pharmaceutically effective amount" of t-PA refers to that amount which provides therapeutic effect in various administration regimens. The compositions hereof may be prepared containing amounts of t-PA at least about 0.1 mg/ml, upwards of about 50 mg/ml, preferably from about 0.4 mg/ml to about 5 mg/ml. For use of these compositions in administration to human patients suffering from myocardial infarctions, for example, these compositions may contain from about 0.4 mg/ml to about 3 mg/ml t-PA, corresponding to the currently contemplated dosage rate for such treatment.

The compositions hereof including lyophilized forms, are prepared in general by compounding the components using generally available pharmaceutical compounding techniques, known per se. Likewise, standard lyophilization procedures and equipment well-known in the art are employed. A particular method for preparing a pharmaceutical composition of t-PA hereof comprises employing purified (according to any standard protein purification scheme) t-PA in any one of several known buffer exchange methods, such as gel filtration. This preferred method was used to isolate and purify the t-PA used as starting material in the stability and solubility studies which follow. The t-PA used in the preferred method was obtained from recombinantly altered Chinese Hamster Ovary Cells (CHO cells) capable of expressing t-PA as a secreted product in the CHO cell culture medium.

DETAILED DESCRIPTION

Applicants have discovered the demonstrative effect that pharmaceutical compositions of t-PA have significantly stabilized biological activity when argininium ion containing buffer is a component and that such formulations do not require sodium chloride for stability, although salt concentrations lower than 0.3M may be employed. In a preferred embodiment, the chloride ion concentration is 0.1M or less. In the neutral pH range, e.g., about pH 6 to 8, the solubility of t-PA is increased by presence of argininium ion such that it is subject to formulation in relatively high concentrations, even without the presence of what the art has regarded as necessary, high stabilizing amounts of salt.

As used herein, the terms "human tissue plasminogen activator", "human t-PA" or "t-PA" denotes human extrinsic (tissue type) plasminogen activator, produced, for example, from natural source extraction and purification (see Collen et al., supra.), and by recombinant cell culture systems as described herein. Its sequence and characteristics are set forth, for example, in European Patent Application Publn. No. 93619, (published 9 Nov. 1983) based upon a first filing on 5 May 1982, incorporated herein by reference. See also Eurpoean Patent Application Publication No. 41766 (published 16 Dec. 1981) based upon a first filing of 11 June 80 and Rijken et al., *Journal of Biol. Chem.* 256, 7035 (1981), also incorporated herein by reference. The terms likewise cover biologically active human tissue plasminogen activator equivalents, differing in one or more amino acids(s) in the overall sequence, or in glycosylation patterns, which are thought to be dependent on the specific culture conditions used and the nature of the host from which the tissue plasminogen activator is obtained.

A. FIGURES

B. LYOPHILIZATION

Lyophilization, or freeze-drying, of the composition is carried out using procedures and equipment well-known to those skilled in the art. Typically, a composition is first frozen to a temperature below its apparent eutectic or collapse temperature. Vacuum is then applied, and heat applied to the lyophilizer shelves, in order to drive off the ice by sublimation, with shelf temperature and chamber pressure adjusted such that the temperature of the frozen mass remains below the apparent eutectic or collapse temperature until essentially all the ice is removed. Following this "primary drying" phase, the shelf temperature may be raised further (with or without a change in chamber pressure) and residual moisture in the freeze-dried cake is driven off.

C. S-2288 ASSAY

A synthetic peptide substrate, S-2288 (H-D-Ile-Pro-Arg-p-nitroanilide·2HCl) is hydrolyzed by t-PA forming colored p-nitroaniline and tripeptide. The maximum differential absorbance between substrate and product (p-nitroaniline) occurs at 405 nm. Production of p-nitroaniline is monitored spectrophotometrically by following absorbance at 405 nm as a function of time. The resulting slope of absorbance versus time is proportional to t-PA activity. This assay is run at 37±0.2° C.

For this assay, 20–100 microliters of a given t-PA sample was added to a 1.2 mL reaction mixture containing 0.33 mM S-2288, 0.067M Tris buffer (pH 7.4), 0.07M NaCl and incubated at 37° C. for 10 minutes. The change in absorbance was monitored for 1 minute and the activity was calculated from the absorbance at 405 nm using the following equation, standardized by the manufacturer:

$$\text{Activity } (IU; \text{ International units}) = \frac{\Delta OD \times 793.65 \text{ (dilution factor)}}{\text{time of incubation} \times \text{sample volume}}$$

D. EXAMPLES

EXAMPLE 1

Purified t-PA was diluted to give a final concentration of 0.2 mg/ml, aliquoted and dialyzed against the buffers shown in Table 1.

TABLE 1

| Dialysis Buffer containing 0.01% Polysorbate 80 | Dialysis Concentration | |
|---|---|---|
| | NaCl | Arginine (as hydrochloride) |
| 1. 0.01 M Sodium Phosphate pH 6, | — | — |
| 2. 0.01 M Sodium Phosphate pH 6, | 0.12 M | 0.2 M |
| 3. 0.01 M Sodium Phosphate pH 6, | — | 0.2 M |
| 4. 0.01 M Sodium Acetate pH 5, | — | — |
| 5. 0.01 M Sodium Acetate pH 5, | 0.12 M | 0.2 M |
| 6. 0.01 M Sodium Acetate pH 5, | | 0.2 M |

After dialysis, the samples were centrifuged and the supernatant lyophilized in 1 ml aliquotes. Lyophilized samples were reconstituted with water and assayed for t-PA activity in the S-2288 assay. Each reconstituted sample was thereafter placed at 37° C. and assayed at various times.

Figure 1:
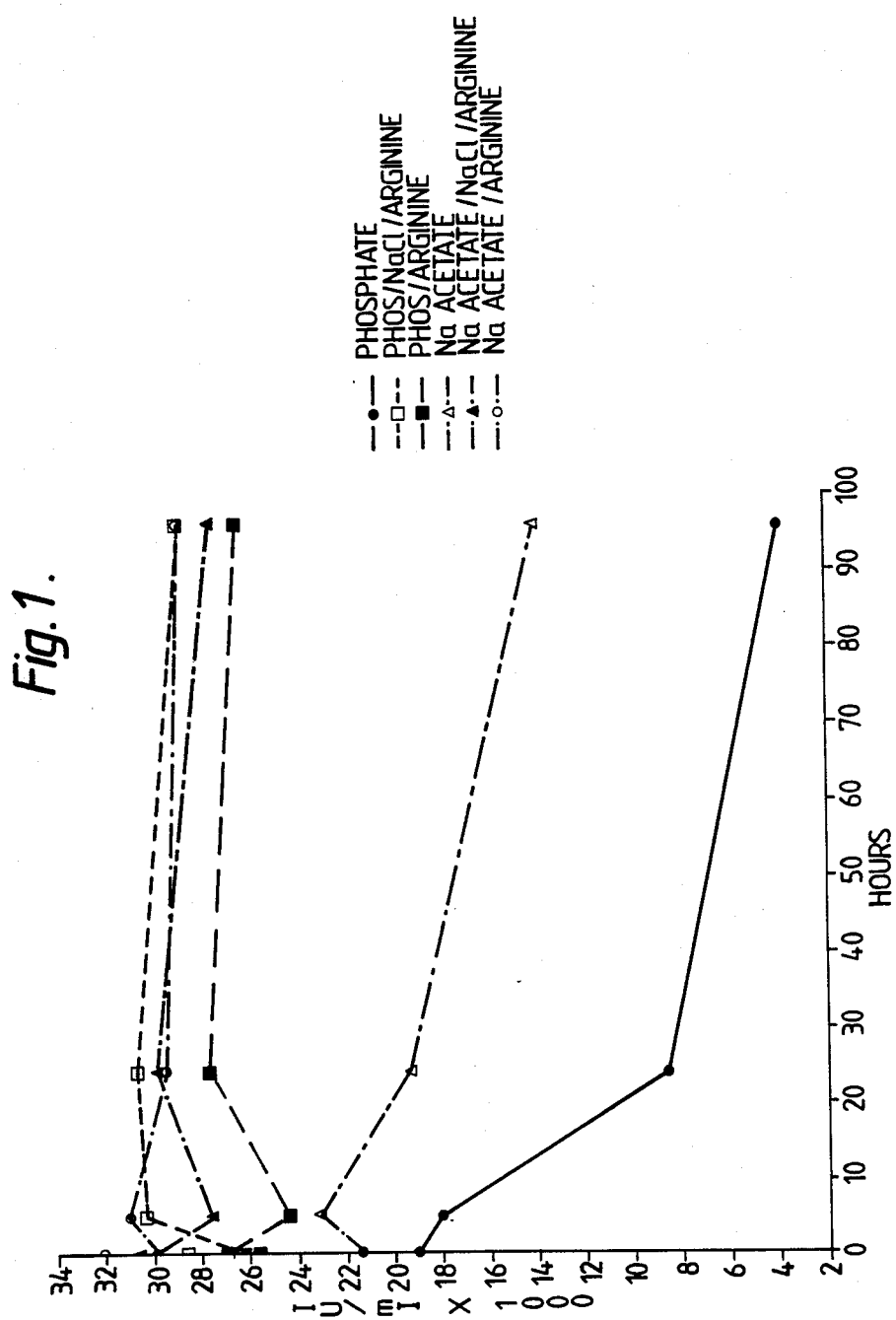
FIG. 1 depicts the stability of t-PA in various formulations.

The results of this experiment are shown in FIG. 1. As can be seen, those systems not containing arginine do not prevent the loss of t-PA activity with time. t-PA activity in those samples containing 0.2M arginine, or 0.2M arginine plus physiological amounts of chloride, retain almost all of the initial t-PA activity after incubation for 4 days at 37° C. These results demonstrate that 0.2M arginine with or without NaCl significantly stabilizes t-PA.

EXAMPLE 2

The stability of t-PA as a function of arginine concentration was determined by measuring the rate of loss of t-PA activity at various temperatures.

Formulation: P1 1.
    0.355 mgs/ml t-PA
    0.05M Na phosphate pH 6.2
    0.05M Arginine as the hydrochloride
2.
    0.498 mgs/ml t-PA
    0.03M Na phosphate pH 6.2
    0.2M Arginine as the hydrochloride 0.5 ml aliquots of solution with the above formulations were aseptically filled into 2 ml glass vials and sealed. The vials were placed at 25°, 37°, 45° C. Two vials of each solution were sampled at 0, 20, 55, and 160 days; and t-PA activity was measured using the S2288 assay. The natural log of the % remaining activity was plotted versus time (days) for each temperature, from which the rate constant was calculated using linear regression analysis.

The rate constants (k) for loss of t-PA stability at two different arginine concentrations and at various temperatures are shown in Table 2.

TABLE 2

Effect of Arginine on t-PA Stability

| Formulation | Arginine | $k\,(day^{-1})$ | | |
|---|---|---|---|---|
| | | 25° C. | 37° C. | 45° C. |
| 0.05 M NaPhosphate, pH 6.2 | 0.05 M | 0.00137 | 0.0102 | 0.0167 |
| 0.03 M NaPhosphate, pH 6.2 | 0.20 M | 0.00043 | 0.00569 | 0.01272 |

As can be seen, 0.2M arginine products rate constants which are smaller than those obtained in 0.05M arginine at each of the indicated temperatures indicating that an increase in arginine concentration increases the stability of t-PA.

EXAMPLE 3

The stability of t-PA is also dependent upon the concentration of non-ionic surfactants. The data are in Table 3.

t-PA was precipitated by dialysis versus 0.01M Na succinate buffer at pH 6.0. The t-PA precipitate was collected from the dialyzed sample by centrifugation. This precipitate was redissolved in the formulation below containing varying concentrations of polysorbate 80.

Formulation:
    0.2M Arginine as the hydrochloride
    0.02M Na phosphate pH 7.2
    Polysorbate 80 (0.0005 to 0.10 percent)

The solutions were aseptically filled into vials and placed at 35° C. and 40° C. Two vials were sampled at each time point and enzymatic activity was assayed using the S2288 assay.

The rate constants were calculated by linear regression analyses of the 10 g (t-PA activity) versus time curve for each temperature, and are shown in Table 3.

TABLE 3

Effect of Polysorbate 80 on t-PA Stability

| Polysorbate 80 % | $k\,(day^{-1})$ | |
|---|---|---|
| | 35° C. | 40° C. |
| 0.0005 | .0055 | .0106 |
| 0.005 | .0049 | .0091 |
| 0.01 | .0043 | .0088 |
| 0.025 | .0040 | .0081 |
| 0.05 | .0041 | .0077 |
| 0.10 | .0037 | .0075 |

This table demonstrates that as the concentration of polysorbate 80 is increased the rate constant (k) decreases. This indicates that more stability is achieved with more polysorbate 80.

EXAMPLE 4 t-PA solutions were prepared by dialysis of purified t-PA versus the argininium phosphate formulation buffer below, followed by dilution with further buffer to the desired final concentration of t-PA.

Formulation buffer:
    0.20M Arginine
    0.18M Phosphoric acid
    0.01% Polysorbate 80 pH 6

Aliquots of each preparation were aseptically filled into 5 or 10 mL vials, lyophilized and sealed. Vials were placed at several temperatures. Two vials per formulation were sampled at each time point and t-PA activity determined by the S2288 assay. The results are in Table 4.

TABLE 4

Stability of t-PA in Lyophilized Formulation

| t-PA (mg/ml)* | pH | Time (mo) | % Remaining (mean of 2 assays ± standard deviation) | | | | |
|---|---|---|---|---|---|---|---|
| | | | 5° C. | 25° C. | 30° C. | 35° C. | 40° C. |
| 1.0 | 6.0 | 2.0 | 102.5 ± 0.0 | 103.3 ± 2.5 | — | 102.6 ± 3.0 | — |
| 2.0 | 6.0 | 2.0 | 111.3 ± 0.7 | 111.1 ± 0.1 | — | 114.6 ± 2.2 | — |
| 5.0 | 6.0 | 2.0 | 112.0 ± 0.3 | 112.7 ± 0.6 | — | 112.3 ± 1.4 | — |
| 1.0 | 6.0 | 3.5 | 98.2 ± 1.3 | — | 96.0 ± 1.7 | — | 97.7 ± 00.1 |

*Concentration of t-PA in solution prior to lyophilization

This data demonstrates that t-PA is stable in the lyophilized form.

EXAMPLE 5

Figure 2:
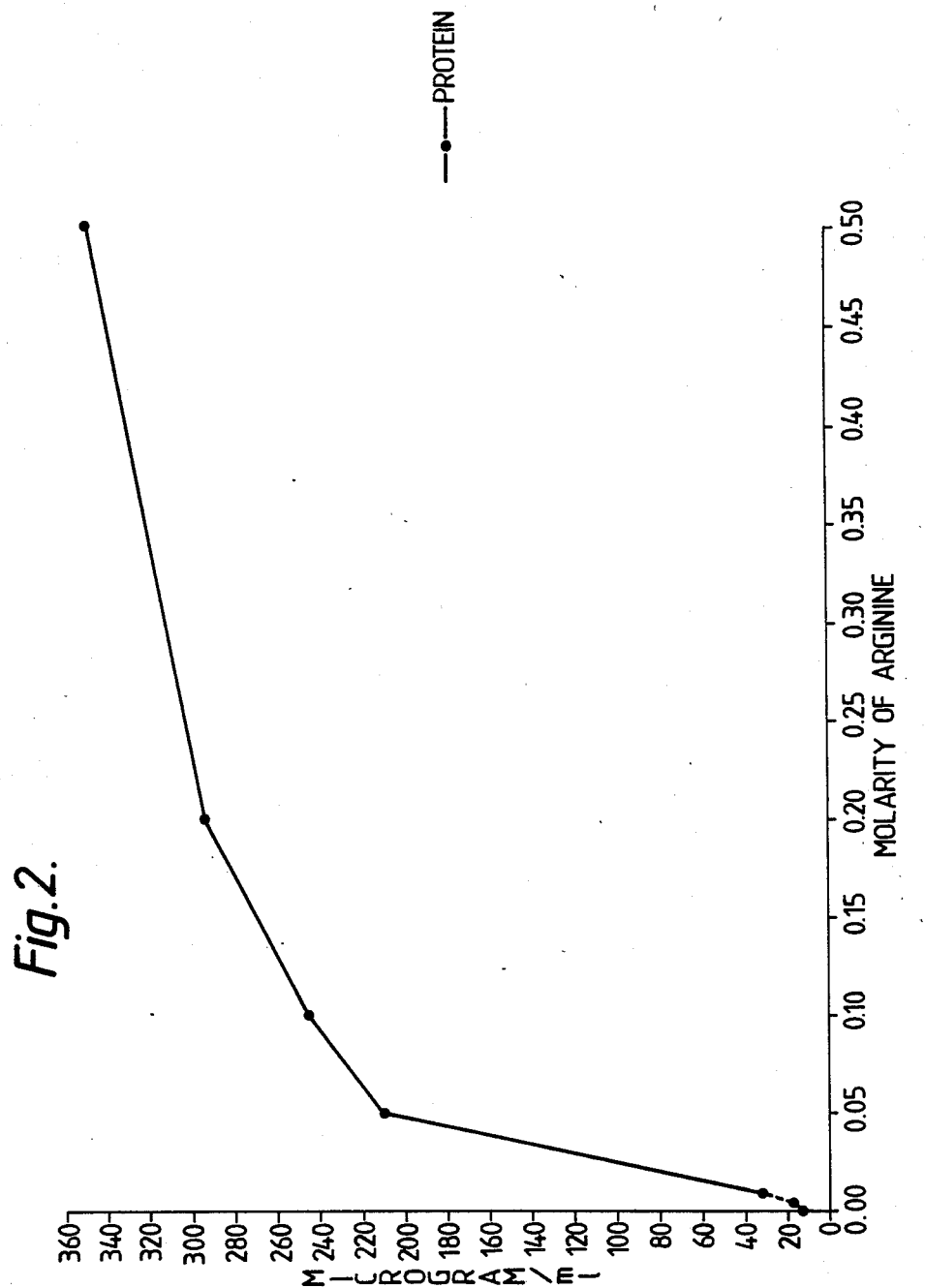
FIG. 2 depicts the effect of arginine concentration on the solubility of t-PA.

A solution containing t-PA at approximately 0.3 to 0.5 mg/ml was dialysed against 10 mM sodium phosphate, pH 7.5, 0.01% polysorbate 80 containing various concentrations of arginine as the hydrochloride. Insoluble material was removed by centrifugation for 2 minutes in an Eppendorf microfuge. The amount of t-PA which remained in solution was assayed in the S-2288 assay. Results are shown in FIG. 2.

As little as 50 mM arginine significantly increases the solubility of t-PA. (The smaller increase in apparent solubility at higher arginine concentrations is an artifact, due to the fact that the original concentration of t-PA in the starting material was only 0.3 to 0.5 mg/ml and thus a limiting solubility was never reached.)

EXAMPLE 6 t-PA was precipitated by dialysis versus 0.001M sodium succinate buffer at pH 6. The resulting precipitate was isolated by centrifugation, then a measured amount of this material was equilibrated in 1 ml of the desired buffer system for 20 hours at 5° C. with agitation. The buffer systems studied were prepared by titration of arginine with phosphoric acid to produce an argininium phosphate system at pH 6.0. Stock solutions were diluted with water to obtain final buffer solutions containing 0.10 to 0.20M arginine (as argininium ion). Following equilibration with the desired buffer system, the resulting t-PA preparation was centrifuged to remove any nonsoluble material, then the supernatants were assayed for soluble t-PA via the S2288 assay.

Figure 3:
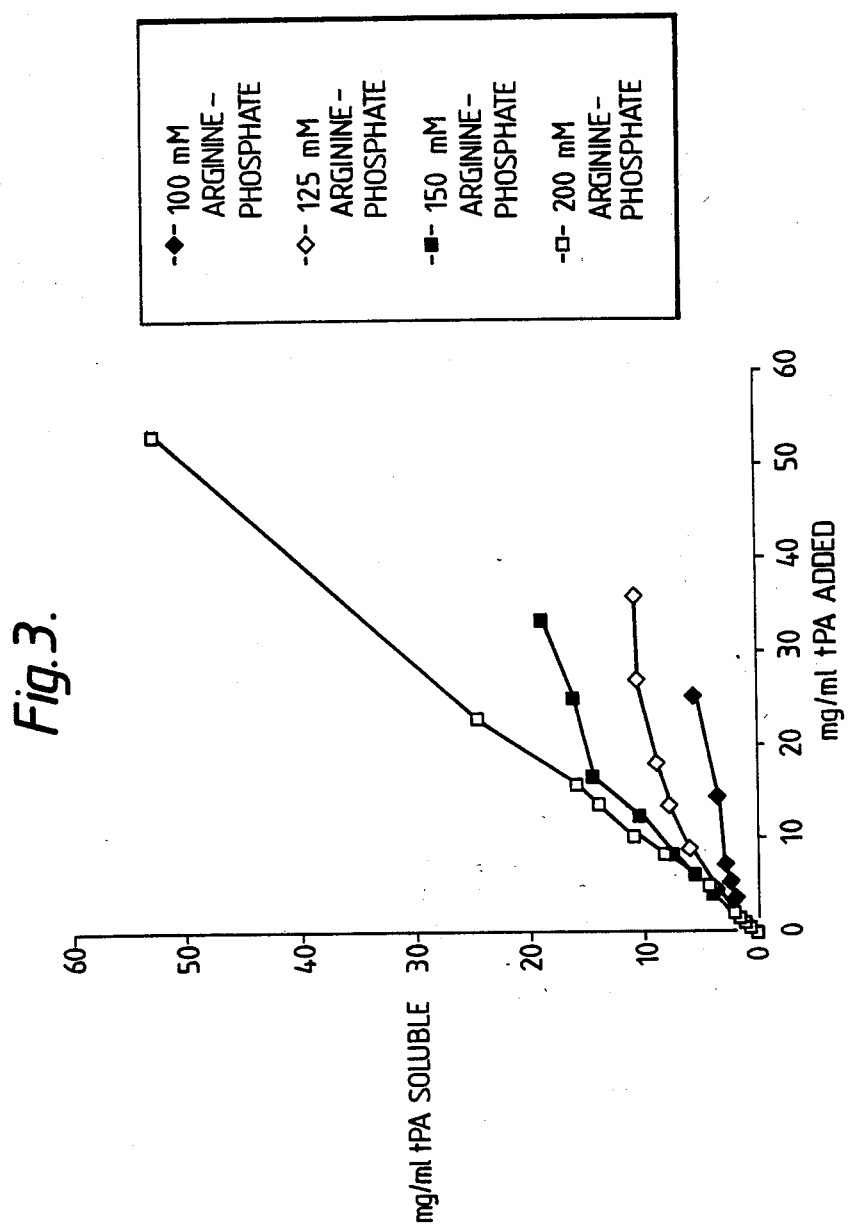
FIG. 3 depicts the solubility limits of t-PA in various concentrations of argininium phosphate buffers at pH 6, 4° C.

Results are shown in FIG. 3. If the t-PA is fully soluble at the concentration of t-PA originally added, then the concentration of soluble t-PA should be the same as that added. Conversely, if the t-PA is not fully soluble at the concentration originally added, then the concentration of soluble t-PA will be less than that added. FIG. 3 shows that t-PA is soluble in 100 mM arginine phosphate pH 6.0 up to about 2 mg/ml, and that at higher argininine phosphate concentration the solubility is markedly enhanced. In particular, at 200 mM arginine phosphate pH 6.0 the t-PA is still fully soluble even at about 54 mg/ml, and clearly the limiting solubility is considerably higher than this.

EXAMPLE 7

The argininium phosphate system below was prepared as a prelyophilization solution.

| Prelyophilization Solution | |
|---|---|
| | mg/ml |
| t-PA | 2.5 |
| L-arginine | 87.1 |
| Phosphoric Acid | 26.8 |
| Polysorbate 80 | 0.1 |
| pH 7.2 | |

Following sterile filtration, approximately 20 ml aliquots were filled in 50 cc vials. Lyophilization was then carried out as follows:

(a) The vials were placed into the lyophilizer and frozen at −50° C. (shelf temperature) under ambient pressure for 10 hours.

(b) Vacuum was applied (chamber pressure of 100 μm Hg) and the shelf temperature raised at 10°/hr. to +7° C., then held at that temperature for 41 hours.

(c) The shelf temperature was then raised to +35° C. and the chamber pressure lowered to 50 μm, and the system held in this state for 14 hours.

The vials were then stoppered, the pressure allowed to return to ambient, and the vials removed from the lyophilizer.

EXAMPLE 8

The effect of sodium chloride on the quality of lyophilized arginine phosphate cakes was investigated. Samples of 0.8M arginine (pH 7) and 0.2M arginine (pH 6) as the phosphate salts were prepared to include concentrations of sodium chloride ranging from 0.01 to 500 nM. 2 mL aliquots of each solution were placed into 10 cc vials and lyophilized using the following cycle:

| Lyophilization Step | Shelf Temperature (Degrees Centigrade) | Chamber Pressure (Microns) | Time (Hours) |
|---|---|---|---|
| Freezing | −45 | Ambient | 10 |
| Primary Drying | Increase at 20°/hr to −35°, then 3°/hr to +35° | 50 | 24 |
| Secondary Drying | +35 | 40 | 26 |

The quality of the resulting cakes are given in Table 5. The data show the formation of pharmaceutically acceptable cakes only with those compositions containing low levels of sodium chloride and that the tolerated low level of sodium chloride is dependent on the arginine concentration.

TABLE 5

Quality of Lyophilized Arginine Buffer System containing Selected Sodium Chloride Concentrations

| Sodium Chloride nM | Cake Quality Initial | | Cake Quality After 2 Months at Room Temperature | |
|---|---|---|---|---|
| | 0.8 M Arginine | 0.2 M Arginine | 0.8 M Arginine | 0.2 M Arginine |
| 500 | Glassy, shrunken mass; no cake | Granular, shrunken mass; no cake | Same as Initial | Same as Initial |
| 100 | White cake; slight melting on cake sides | White cake with glassy appearance | Same as Initial | Glassy film on vial bottom; no cake |
| 50 | White cake; glassy edges slightly shrunken | White cake with glassy appearance | Same as Initial | Glassy to white mass on vial. bottom |
| 10 | White cake; slightly shrunken | White cake very much shrunken | Same as Initial | White mass in vial |
| 1 | White cake; very slightly shrunken | White cake; very much shrunken | Same as Initial | Further shrunken |
| 0.1 | White cake; very slightly shrunken | White cake; very much shrunken | Same as Initial | Further shrunken |
| 0.01 | White cake; very slightly shrunken | White cake; very much shrunken | Same as Initial | Slight additional shrinkage |

It will occur to those ordinarily skilled in the art that various modifications may be made to the disclosed embodiments and that such modifications are intended to be within the scope of the present invention.

What is claimed is:

1. A pharmaceutical composition comprising a pharmaceutically effective amount of human tissue plasminogen activator and a pharmaceutically acceptable argininium ion containing buffer, said composition having a chloride ion concentration of less than about 0.3M, and a pH of approximately 5.

2. A frozen composition according to claim 1.

3. A composition according to claim 2 that is converted to lyophilized form.

4. A freeze-dried composition that results from lyophilization of a frozen composition according to claim 2.

5. A composition according to claim 3 or claim 4 wherein said lyophilized form is reconstituted.

6. A composition according to claim 1 wherein said argininium buffer is other than argininium chloride.

7. A composition according to claim 1 wherein said buffer is provided by argininium ion and a counterion capable of adjusting the collapse temperature of the composition to a readily lyophilizable state.

8. A composition according to claim 7 wherein said counterion is selected from the group consisting of citrate, phosphate, tartrate, sulfate, malate, meleate and succinate.

9. A composition according to claim 7 wherein said counterion is selected from the group consisting of citrate and phosphate.

10. A composition according to claim 7 wherein said counterion is phosphate.

11. A composition according to claim 1 wherein said human tissue plasminogen activator has a concentration of at least about 0.1 mg/ml and said argininium ion has a concentration of about 0.05 to about 1.0M.

12. A composition according to claim 1 wherein said human tissue plasminogen activator has a concentration of at least about 0.4 to about 5.0 mg/ml and said argininium ion has a concentration of about 0.1 to about 0.5M.

13. A composition according to claim 1 wherein said composition is diiluted with a pharmaceutically acceptable diluent.

14. A composition according to claim 1 wherein said composition contains a non-ionic detergent comprising about 0.001 to 1% of said composition.

15. A method for the preparation of the composition of claim 1 comprising the steps of compounding said t-PA and argininium ion containing buffer.

16. A method further to claim 15 comprising lyophilizing said composition.

17. A pharmaceutical composition comprising a pharmaceutically effective amount of human tissue plasminogen activator and a pharmaceutically acceptable argininium ion containing buffer, said composition having a chloride ion concentration of less than about 0.3M, and a pH of approximately 6.

* * * * *